(12) United States Patent
Ramzipoor

(10) Patent No.: US 7,771,451 B2
(45) Date of Patent: Aug. 10, 2010

(54) METHOD AND APPARATUS FOR THE DEPLOYMENT OF VASO-OCCLUSIVE COILS

(75) Inventor: Kamal Ramzipoor, Fremont, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1103 days.

(21) Appl. No.: 11/278,768

(22) Filed: Apr. 5, 2006

(65) Prior Publication Data
US 2007/0239191 A1  Oct. 11, 2007

(51) Int. Cl.
*A61M 29/00* (2006.01)
(52) U.S. Cl. .................. 606/200; 606/108
(58) Field of Classification Search ................ 623/1.11; 606/191, 200
See application file for complete search history.

(56) References Cited

U.S. PATENT DOCUMENTS

| | | | |
|---|---|---|---|
| 4,994,069 A | 2/1991 | Ritchart et al. | |
| 5,108,407 A * | 4/1992 | Geremia et al. | 606/108 |
| 5,122,136 A | 6/1992 | Guglielmi et al. | |
| 5,226,911 A | 7/1993 | Chee et al. | |
| 5,234,437 A | 8/1993 | Sepetka | |
| 5,250,071 A | 10/1993 | Palermo | |
| 5,261,916 A | 11/1993 | Engelson | |
| 5,304,194 A | 4/1994 | Chee et al. | |
| 5,304,195 A | 4/1994 | Twyford, Jr. et al. | |
| 5,354,295 A | 10/1994 | Guglielmi et al. | |
| 5,382,259 A | 1/1995 | Phelps et al. | |
| 5,549,624 A | 8/1996 | Mirigian et al. | |
| 5,578,074 A * | 11/1996 | Mirigian | 606/108 |
| 5,690,666 A | 11/1997 | Berenstein et al. | |
| 5,716,410 A * | 2/1998 | Wang et al. | 606/191 |
| 5,853,418 A | 12/1998 | Ken et al. | |
| 6,042,589 A * | 3/2000 | Marianne | 606/108 |

(Continued)

FOREIGN PATENT DOCUMENTS

EP   1537838   6/2005

(Continued)

OTHER PUBLICATIONS

PCT International Search Report for PCT/US2007/065389, Applicant Boston Scientific Corporation, Forms PCT/ISA/210 and 220, Dated Oct. 15, 2007 (5 pages).

(Continued)

*Primary Examiner*—Todd E Manahan
*Assistant Examiner*—Erin Colello
(74) *Attorney, Agent, or Firm*—Vista IP Law Group LLP (57) ABSTRACT

A vaso-occlusive delivery device includes an elongate delivery member which may take the form of a core wire. An actuating member is disposed at or adjacent to the distal end of the delivery member. The actuating member includes an electroactive polymer that can be selectively biased to an expanded or non-expanded state by application of direct current of different polarities. A vaso-occlusive device such as a coil may be detachably secured to the delivery device by expanding the actuating member within a proximal end of the coil to form an interference or friction fit using a first direct current polarity. The coil may be disengaged from the delivery member by application of direct current of a second, opposite polarity.

7 Claims, 4 Drawing Sheets

U.S. PATENT DOCUMENTS

| | | | |
|---|---|---|---|
| 6,165,178 | A | 12/2000 | Bashiri et al. |
| 6,277,126 | B1 * | 8/2001 | Barry et al. ................. 606/108 |
| 6,280,457 | B1 | 8/2001 | Wallace et al. |
| 6,296,622 | B1 * | 10/2001 | Kurz et al. ............... 604/93.01 |
| 6,478,773 | B1 * | 11/2002 | Gandhi et al. ............... 604/113 |
| 6,514,237 | B1 | 2/2003 | Maseda |
| 6,969,395 | B2 * | 11/2005 | Eskuri ....................... 606/200 |
| 7,166,122 | B2 * | 1/2007 | Aganon et al. .............. 606/200 |
| 7,179,276 | B2 * | 2/2007 | Barry et al. ................. 606/200 |
| 7,182,774 | B2 * | 2/2007 | Barry et al. ................. 606/200 |
| 7,582,101 | B2 * | 9/2009 | Jones et al. ................. 606/200 |
| 2003/0236531 | A1 * | 12/2003 | Couvillon, Jr. ............. 606/113 |
| 2004/0002733 | A1 | 1/2004 | Teoh |
| 2004/0106933 | A1 * | 6/2004 | Barry et al. ................. 606/108 |
| 2004/0220585 | A1 * | 11/2004 | Nikolchev .................. 606/108 |
| 2005/0102017 | A1 * | 5/2005 | Mattison .................... 623/1.11 |
| 2005/0149108 | A1 * | 7/2005 | Cox ........................... 606/200 |
| 2005/0165439 | A1 * | 7/2005 | Weber et al. ................ 606/191 |
| 2006/0235457 | A1 * | 10/2006 | Belson ....................... 606/191 |
| 2006/0253149 | A1 * | 11/2006 | Gandhi et al. ............... 606/200 |

FOREIGN PATENT DOCUMENTS

EP      1537838 A1 *  6/2005

OTHER PUBLICATIONS

PCT Written Opinion of the International Search Authority for PCT/US2007/065389, Applicant Boston Scientific Corporation, Forms PCT/ISA/237, dated Oct. 15, 2007 (7 pages).

PCT International Search Report for PCT/US2005/001854, Applicant Boston Scientific Corporation, Forms PCT/ISA/210, dated May 9, 2005 (3 pages).

* cited by examiner

METHOD AND APPARATUS FOR THE DEPLOYMENT OF VASO-OCCLUSIVE COILS

FIELD OF THE INVENTION

The field of the invention generally relates to implantable vaso-occlusive devices. More particularly, the field of the invention pertains to vaso-occlusive coils that are deployed within a vascular space such as, for example, an aneurysm.

BACKGROUND OF THE INVENTION

Vaso-occlusion devices are surgical implements or implants that are placed within the vasculature of the human body, typically via a catheter, to block the flow of blood through a vessel or an aneurysm stemming from the vessel. Virtually all such vaso-occlusive implants are delivered by pushing the devices through wire-guided catheters.

One widely used vaso-occlusive device is a helical wire coil having windings that may be dimensioned to engage the walls of an aneurysm. For example, a vaso-occlusive device such as a helical wire coil may be positioned within the aneurysm space to cause or accelerate the formation of a clot and later-formed collagenous mass. The resulting occlusion fills and seals the aneurysm, thereby preventing the weakened wall of the aneurysm from being exposed to the oscillating blood pressure of the open vascular lumen. The use of vaso-occlusive coils for the treatment of aneurysms is a significant improvement over alternative surgical methods.

One common vaso-occlusive device is formed from a generally soft, helically wound coil. The coil may be formed by winding a wire (e.g., a platinum wire) about a primary mandrel and applying a heat treatment to impart a primary winding coil shape. The relative stiffness of the coil will depend on, among other factors, the diameter of the wire strand, the diameter of the primary mandrel, and the pitch of the primary windings. As an example of an early vaso-occlusive device, U.S. Pat. No. 4,994,069, describes a vaso-occlusive coil that assumes a primary, linear helical configuration when stretched and a folded, and a secondary, convoluted configuration when relaxed in a minimal energy configuration. The coil assumes the stretched condition during delivery of the coil at the desired site by passage through the catheter, and assumes the relaxed configuration, which is better suited to occlude the aneurysm, once the device is deployed.

There are a variety of ways of discharging vaso-occlusive coils into the human vasculature. In some devices, vaso-occlusive coils are deployed from a delivery wire using a mechanical detachment mechanism. For instance, U.S. Pat. No. 5,234,437 illustrates a method of unscrewing a helically wound coil from a pusher having interlocking surfaces. Alternatively, U.S. Pat. No. 5,250,071 shows an embolic coil assembly that uses interlocking clasps mounted on the pusher and on the embolic coil. In still another design, U.S. Pat. No. 5,261,916 shows a detachable pusher-vaso-occlusive coil assembly having an interlocking ball and keyway-type coupling. U.S. Pat. No. 5,304,195 shows a pusher-vaso-occlusive coiled assembly having an affixed, proximally extending wire carrying a ball on its proximal end and a pusher having a similar end. The two ends are interlocked and disengage when expelled from the distal tip of the delivery catheter.

Still other vaso-occlusive coils utilize an electrolytically-severable joint to release vaso-occlusive coils at the site of interest. For example, U.S. Pat. Nos. 5,354,295 and 5,122,136 disclose a device that uses an electrolytically-severable joint to place a finely wound platinum coil into a vascular cavity such as an aneurysm. The coil is delivered endovascularly using a delivery member such as a delivery catheter. After placement in the aneurysm, the coil is severed from a proximally located insertion core wire by the application of a small electric current to the core wire. The joint connecting the coil to the core wire is then electrolytically degraded to release the vaso-occlusive coil within the aneurysm.

While a variety of detachment modalities exist for vaso-occlusive members, there is a continuing need in the art for alternative detachment mechanisms.

SUMMARY OF THE INVENTION

The present invention is directed to a vaso-occlusive delivery system or device capable of delivering an occlusion member (e.g., a helically wound coil) to a vascular space such as an aneurysm.

In one aspect of the invention, a vaso-occlusive delivery device includes an elongate delivery member. The elongate delivery member may take the form of a core wire. An actuating member is disposed at or adjacent to the distal end of the delivery member. The actuating member includes an electroactive polymer (EAP) that can be selectively biased to an expanded or non-expanded state by application of direct current of different polarities. A vaso-occlusive device such as a coil may be detachably secured to the delivery device by expanding the actuating member within a proximal end of the coil to form an interference or friction fit by application of a direct current having a first polarity (eg. positive or negative). The coil may be disengaged from the delivery member by application of direct current of a second, opposite polarity.

In another aspect of the invention, a vaso-occlusive delivery device includes an elongate delivery member having a distal end and an actuating member disposed at or adjacent to the distal end of the elongate delivery member. The actuating member includes an electroactive polymer (EAP) that can be biased or toggled between first and second states based on the application of direct current of different polarities. For example, the first state may be an expanded state that created when direct current of a first polarity is applied to the actuating member. The second state may be a non-expanded state that is formed when direct current of a second, opposite polarity is applied to the actuating member. The bi-state nature of the actuating member may be used to selectively engage/disengage a vaso-occlusive device such as a coil.

In one aspect of the invention, the coil includes a tubular member that is disposed at or adjacent to a proximal end of the coil. The tubular member may be contained within a proximally-located lumen of the coil. To secure the elongate delivery member to the coil the actuating member is disposed within the tubular member (e.g., within a lumen or space of the tubular member). When the actuating member is biased to a first biased state (e.g., an expanded state), the actuating member forms an interference or friction fit with an inner surface of the tubular member. When the actuating member is biased to a second biased state (e.g., non-expanded state), the actuating member is detached from the tubular member. Upon detachment of the actuating member from the tubular member, the coil is free from the elongate delivery member and the coil transitions to its relaxed state within the vascular space (e.g., aneurysm).

The actuating member may take the form of a radially expandable ring located about the periphery of the elongate delivery member. In one alternative aspect of the invention, the actuating member includes an actuating ring or base on which an electroactive polymer layer is located. The actuating ring or base may be made from an electrically conductive material such as, for instance, a metallic material.

In another alternative aspect of the invention, the actuating member is formed as a bilayer member formed from two different materials. One layer of the bilayer member is formed from an electroactive polymer. In response to the application of different polarities of direct current, the bilayer member is toggled or switchable between open and closed states.

In one aspect of the invention, a vaso-occlusive delivery device includes an elongate delivery member having a distal end. A bilayer member is disposed at or adjacent to the distal end of the elongate delivery member. The bilayer member has one layer formed from a first material and a second layer formed from an electroactive polymer. When direct current of a first polarity is applied to the bilayer member, the bilayer member is biased to a first state (e.g., closed). Conversely, when direct current of a second, opposite polarity is applied to the bilayer member, the bilayer member is biased to a second state (e.g., open).

In still another aspect of the invention, the bilayer member frictionally engages a mating member disposed on a proximal end of a coil. The bilayer member secures the coil to the elongate delivery member in the closed state while the bilayer member detaches from the coil (e.g., via a mating member) in the open state.

In still another aspect of the invention, a method of loading a vaso-occlusive device onto a delivery member includes the steps of inserting an actuating member containing the electroactive polymer within a lumen of the coil. The actuating member is then activated by application of direct current to secure the coil to the delivery member. In one aspect, the actuating member frictionally engages a tubular member contained inside a lumen in the proximal end of the coil.

In still another aspect of the invention, a method of detaching a vaso-occlusive device from a delivery member includes the steps of activating an actuating member containing the electroactive polymer by applying a direct current thereto. In one aspect of the invention, the applied direct current has a polarity opposite to that used to secure the coil to the delivery member. Upon application of this direct current, the actuating member decreases its effective diameter such that the coil and delivery member are detached from one another.

It is thus one object of the invention to provide a device and method for deploying or discharging a vaso-occlusive coil within vascular space such as, for example, an aneurysm. It is another object of the invention to provide an actuation mechanism for deploying one or more vaso-occlusive members from a delivery member such as a core wire. It is still another object of the invention to provide a device and method that utilizes an electroactive polymer to selectively engage or disengage a vaso-occlusive device such as a coil. Further features and advantages will become apparent upon review of the following drawings and description of the preferred embodiments.

DETAILED DESCRIPTION OF THE PREFERRED EMBODIMENTS

Figure 1:
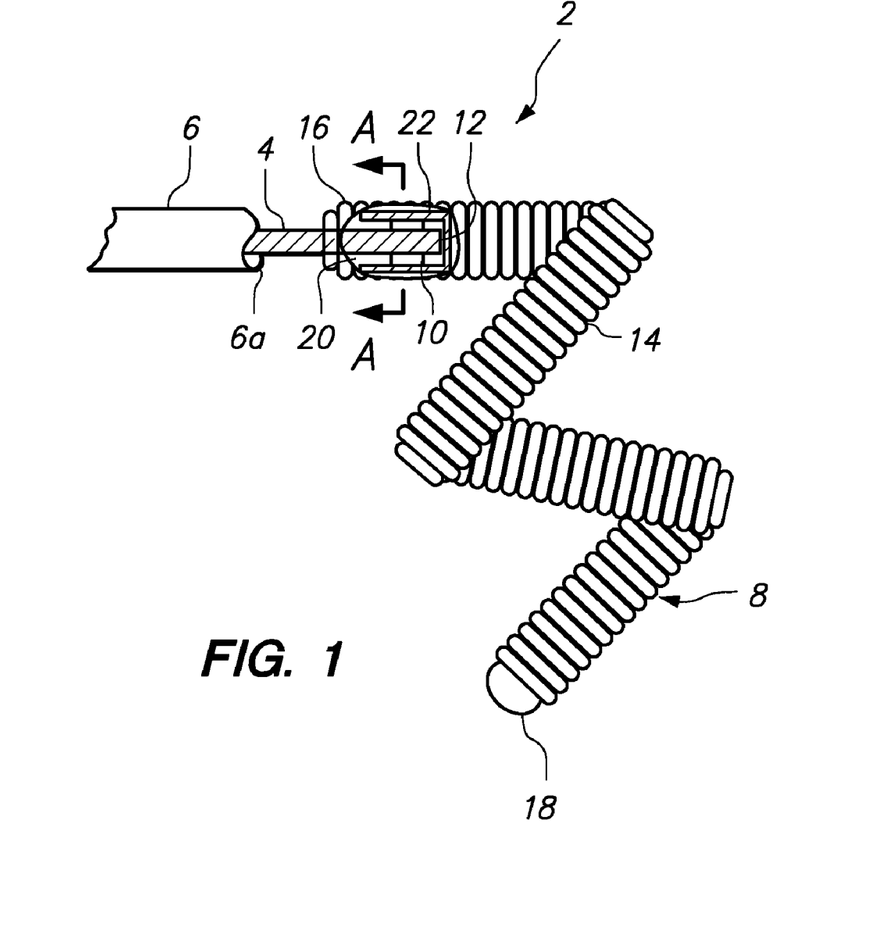
FIG. 1 illustrates a vaso-occlusive delivery device according to one aspect of the invention. A vaso-occlusive coil is shown attached to an elongate delivery member via an actuating member. A portion of the coil is removed to illustrate the interface or friction fit between the actuating member and the coil.

FIG. 1 illustrates a vaso-occlusive delivery device 2 constructed in accordance with one embodiment of the invention. The vaso-occlusive delivery device 2 includes an elongate delivery member 4 which may take the form of a core wire or the like. The elongate delivery member 4 may be contained within a lumen formed in a flexible elongate member such as a catheter 6. The elongate delivery member 4 is axially moveable within the catheter 6. A lubricous coating or the like on either the catheter 6 or the elongate delivery member 4 may be used to facilitate the pushability of the elongate delivery member 4. As seen it FIG. 1, the elongate delivery member 4 is shown attached or otherwise secured to a vaso-occlusive device 8 such as a coil 14.

The delivery member 4 includes an actuating member 10 disposed at or adjacent to the distal end 12 thereof. The actuating member 10 is wholly or at least partially formed from an electroactive polymer (EAP). Electroactive polymers are a class of polymers characterized by their ability to change shape in response to electrical stimulation.

EAPs that may be used in connection with the present invention may be ionic EAPs, more typically conductive EAPs that feature a conjugated backbone (e.g., they have a backbone that comprises and alternating series of single and double carbon-carbon bonds). Some exemplary known EAPs are polypyrroles, polyanilines, polythiophenes, polyethylenedioxythiophenes, poly(p-phenylene vinylene)s, polysulfones and polyacetylenes. Polypyrrole, which is one of the most stable of these polymers under physiological conditions, may be used as part of the actuating member 10.

EAPs are typically semi-conductors in their purified form. However, upon oxidation or reduction of the polymer, the electrical conductivity is understood to be changed from a semi-conductive regime to a semi-metallic regime. Such oxidation and reduction are believed to lead to a charge imbalance that, in turn, results in a flow of ions into or out of the EAP material. The ions typically enter/exit the material from/ into an ionically conductive electrolyte medium associated with the electroactive polymer. The electrolyte medium may be artificially generated or, alternatively, the electrolyte medium may be naturally occurring (e.g., blood or other bodily fluids)

Generally, the mass transfer of ions into and out of the EAP material leads to an expansion (or contraction) of the polymer. Ionic EAP-based materials also have a number of additional properties that make them attractive for use in the devices of the present invention, including the following: (a) they are lightweight, flexible, small and easily manufactured; (b) energy sources are available which are easy to control, and energy can be easily delivered to the EAPS; (c) small changes in potential (e.g., potential changes on the order of 1V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using semiconductor-based processing techniques (e.g., photolithography).

As explained in more detail below, the EAP-based actuating member 10 is actuated to switch or toggle between two biased states. In one biased state, the actuating member 10 is non-expanded. In a second biased state, the actuating member 10 is expanded.

In order to actuate or toggle the actuating member 10 between the two states, electrical current is delivered to the actuating member 10. For example, a current source (not shown) external to the vaso-occlusive device 2 may be used. The current may be delivered via the delivery member 4 (e.g., core wire) or a separate conductor (not shown). A counter electrode may also be used to complete the circuit formed with the actuating member 10. For example, a counter electrode in the form of a patch or the like may be affixed to the patient's skin.

The counter electrode may be formed from any suitable electrical conductor, for example, a conducting polymer, a conducting gel, or a metal, such as stainless steel, gold or platinum. Typically, at least a portion of the surface of the counter electrode is generally in contact with and electrolyte, in order to provide a return path for electrons.

The actuating member 10 may be activated within the presence of an ionic environment. In this regard, an electrolyte or other ionic solution allows for the flow of ions and thus acts as a source/sink for the ions. The electrolyte may be, for example, a liquid, a gel, or a solid, so long as ion movement is permitted. In the case where the electrolyte is a liquid, it may be, for example, an aqueous solution containing a salt, for example, an NaCl solution, a KCl solution, a sodium dodecylbenzene sulfonate solution, a phosphate buffered solution, physiological fluid, and the like. Where the electrolyte is a gel, it may be, for example, a salt-containing agar gel or polymethylmethacrylate (PMMA) gel. Where the electrolyte is a solid, it may be, for example, a polymer electrolyte.

In accordance with certain embodiments of the invention, actuating member 10 may be integrated directly in the delivery member 4. Alternatively, the actuating member 10 may be formed separately and later affixed to the delivery member 4. For example, the actuating member 10 may be formed on an intermediate member 24 (e.g., actuating ring discussed in more detail below) that is then secured to the delivery member 4. The intermediate member 24 may then be secured to the delivery member 4 by a friction fit, through the use of an adhesive, or by brazing, welding, or other similar technique.

In the case of a polypyrrole-based actuating member 10, the portion containing the polypyrrole polymer may be fabricated using a number of known techniques, for example, extrusion, casting, dip coating, spin coating or electro-polymerization/deposition techniques. Polypyrrole-containing active regions can also be patterned, for example, using lithographic techniques, if desired.

Still referring to FIG. 1, the vaso-occlusive device 8 has an outer primary coil 14 that has a proximal end 16 and a distal end or tip 18. A lumen 20 extends between the proximal end 16 and distal end 18 of the primary coil 14. The materials used in constructing the primary coil 14 may be any of a wide variety of materials, and preferably, a radio-opaque material such as a metal or a polymer. Suitable metals and alloys for the wire making up the primary coil 14 include the Platinum Group metals, especially platinum, rhodium, palladium, rhenium, as well as tungsten, gold, silver, tantalum, and alloys of these metals. In addition to being largely biologically inert, these metals have significant radio-opacity and their alloys may be tailored to accomplish an appropriate blend of flexibility and stiffness. One illustrative example is a platinum/tungsten alloy, e.g., 8% tungsten and the remainder platinum.

The primary coil 14 may also be made of radiolucent fibers or polymers (or metallic threads coated with radiolucent or radio-opaque fibers) such as DACRON (polyester), polyglycolic acid, polylactic acid, fluoropolymers (polytetrafluoroethylene), Nylon (polyamide), or even cotton or silk. If a polymer is used as the major component of the primary coil 14, it is desirably filled with some amount of radio-opaque material such as powdered tantalum, powdered tungsten, bismuth oxide, barium sulfate, and the like.

When manufacturing the primary coil 14, the coil material is wound into a coil, which will typically be linear. Generally speaking, when the coil 14 is a metallic coil made from a platinum alloy or a super-elastic alloy such as titanium/nickel alloy, known as "NITINOL". The diameter of the wire used in the production of the coils may fall in the range of about 0.00025 inches to about 0.006 inches. The coil 14 may have a primary diameter of between about 0.003 and about 0.025 inches, but for most neurovascular applications, a diameter between about 0.008 to about 0.018 inches provides sufficient hoop strength to hold the primary coil 14 in place within the chosen body site, lumen, or cavity, without substantially distending the wall of the site and without moving from the site as a result of the repetitive fluid pulsing found in the vascular system.

The axial length of the coil wire will usually fall in the range of around 0.5 to around 100 cm, more usually around 2.0 to 40 cm. Depending upon usage, the coil 14 may well have 10-75 turns per centimeter, preferably 10-40 turns per centimeter. Of course, all of the dimensions provided above should be viewed only as guidelines, and the invention, in its broader aspects, should not be limited thereto. Dimensions that are suitable for use in occluding sites within the human body are included in the scope of this invention.

Depending on the desired therapeutic effect and the shape of the site to be treated, the primary coil 14 may later be treated or accessorized in numerous ways in order to enhance its therapeutic effect. The primary coil 14 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 14 may have (little or no shape after introduction into the vascular space, as disclosed in U.S. Pat. No. 5,690,666, the entirety of which is expressly incorporated by reference herein. In addition, external materials may be added to the outside of the primary coil 14 in an effort to increase its thrombolytic properties. These alternative embodiments are disclosed in U.S. Pat. Nos. 5,226,911, 5,304,194, 5,549,624, and 5,382,259, the entireties of which are expressly incorporated herein by reference, and U.S. Pat. No. 6,280,457, the entirety of which has previously been incorporated by reference.

Figure 1A:
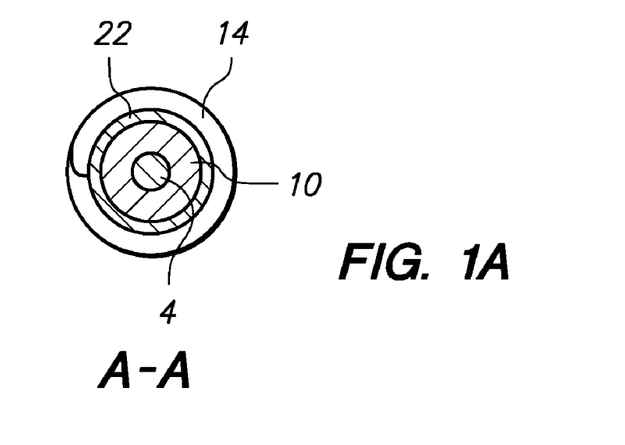
FIG. 1A is a cross-sectional view of the delivery member and attached coil taken along the line A-A in FIG. 1.

Referring to FIGS. 1 and 1A, a tubular member 22 is secured with the proximal end 16 of the primary coil 14 within the coil lumen 20. As seen in FIG. 1, the tubular member 22 engages or is otherwise secured to an interior surface of the primary coil 14. The tubular member 22 thus acts as a contact or anchoring surface for the actuating member 10.

FIGS. 1 and 1A illustrate the actuating member 10 in the biased, expanded state. In this regard, the effective diameter of the actuating member 10 increases or expands and an outer surface thereof contacts the inner surface of the tubular member 22. The expansion of the actuating member 10 forms a friction or interference fit between the actuating member 10 and the tubular member 22 and, consequently, the coil 14.

Figure 2:
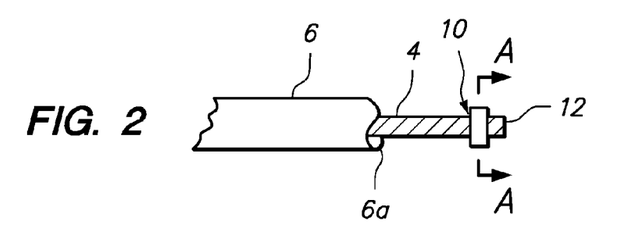
FIG. 2 is a side view of an elongate delivery member according to one aspect of the invention. The distal end of the delivery member is shown with an actuating member in a biased, non-expanded state.
Figure 2A:
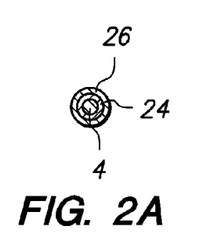
FIG. 2A is a cross-sectional view of the actuating member and delivery member taken along the line A-A in FIG. 2.

FIGS. 2 and 2A illustrate views of the delivery member 4 with the actuating member 10 biased in the non-expanded state. In addition, the actuating member 10 is shown having an intermediate member 24 interposed between the delivery member 4 and an EAP layer 26. The intermediate member 24 may take the form of a actuating ring or the like. In one aspect of the invention, the intermediate member 24 is formed from a metallic material capable of conducting electricity. The EAP layer 26 may then be deposited on the exterior surface of the intermediate member 24.

Referring back to FIGS. 1 and 1A, to form the assembled delivery device 2 with the delivery member 4 attached to the vaso-occlusive device 8, the actuating member 10 in the non-expanded state (e.g. as shown in FIGS. 2 and 2A) is inserted into the lumen 20 of the proximal end 16 of the coil 14. While the actuating member 10 is immersed in an ionic environment (e.g., in the presence of electrolytes), the actuating member 10 is then activated by application of a direct current of a first polarity (e.g., positive or negative). The application of direct current to the actuating member 10 causes radial expansion of the EAP layer 26. The EAP layer 26 is then biased to a second, expanded state.

Figure 3:
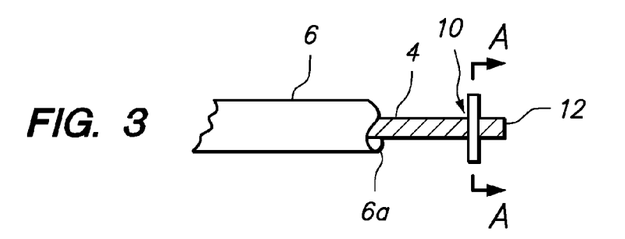
FIG. 3 is a side view of an elongate delivery member according to another aspect of the invention. The distal end of the delivery member is shown with an actuating member in a biased, expanded state.
Figure 3A:
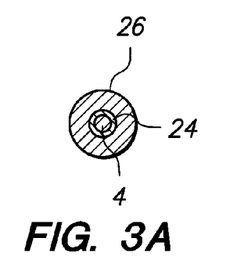
FIG. 3A is a cross-sectional view of the actuating member and delivery member taken along the line A-A in FIG. 3.

FIGS. 3 and 3A illustrate the radial expansion of the EAP layer 26 after application of a biasing electrical current. Expansion of the EAP layer 26 increases the effective diameter of the actuating member 10 to create the interference or friction fit with the coil 14. As seen in FIGS. 3 and 3A expansion of the EAP layer 26 may cause a reduction or shortening of the width of the EAP layer 26. The decrease in the width of the EAP layer 26, however, is accompanied by an increase in the effective diameter of the EAP layer 26. The EAP layer 26 undergoes radial expansion until contact is made with an anchoring surface such as, for example, an inner surface of tubular member 22.

Figure 4:
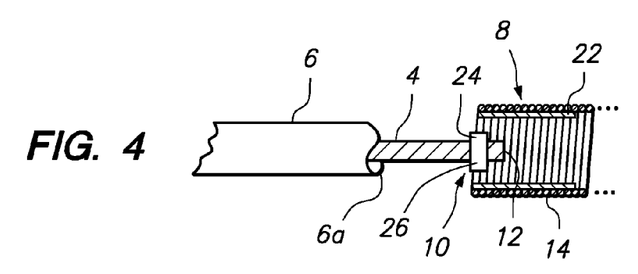
FIG. 4 is a side view of an elongate delivery member being positioned within a proximal lumen of a coil. The coil is partially shown to illustrate the actuating member in the biased non-expanded state.
Figure 5:
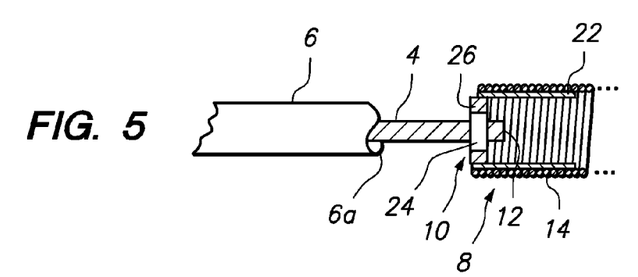
FIG. 5 is a side view of an elongate delivery member being positioned within a proximal lumen of a coil. The coil is partially shown to illustrate the actuating member in the biased, expanded state.

FIGS. 4 and 5 illustrate a vaso-occlusive device 8 being loaded or secured to a delivery member 4. First, as shown in FIG. 4, a delivery member 4 having the actuating member 10 in the non-expanded state is inserted into the lumen 20 of the coil 14. The actuating member 10 is then actuated by application of a direct current of a first polarity (e.g., positive or negative). The EAP layer 26 on the intermediate member 24 then expands in the radial direction and engages the inner surface of the tubular member 22. A friction or interference fit is thus formed between the delivery member 4 and the coil 14.

Figure 11:
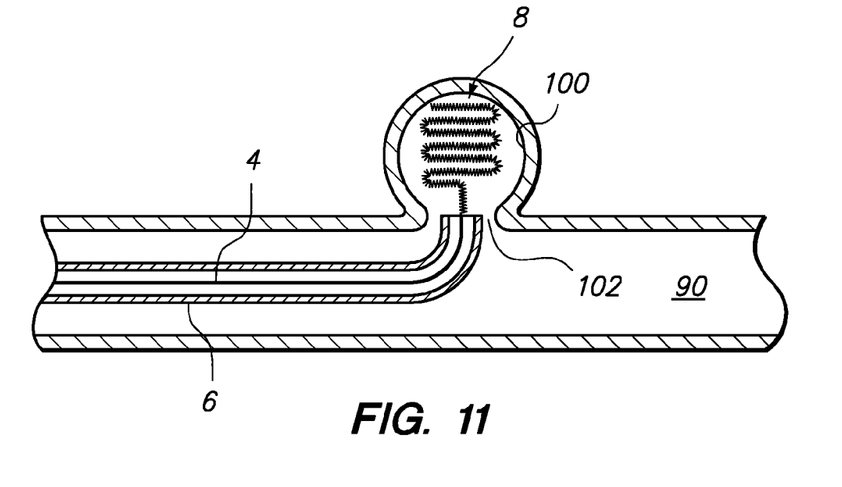
FIG. 11 is a cross-sectional side view of a vascular region having an aneurysm therein. A delivery member is shown deploying a vaso-occlusive coil within the space defining the aneurysm.
Figure 12:
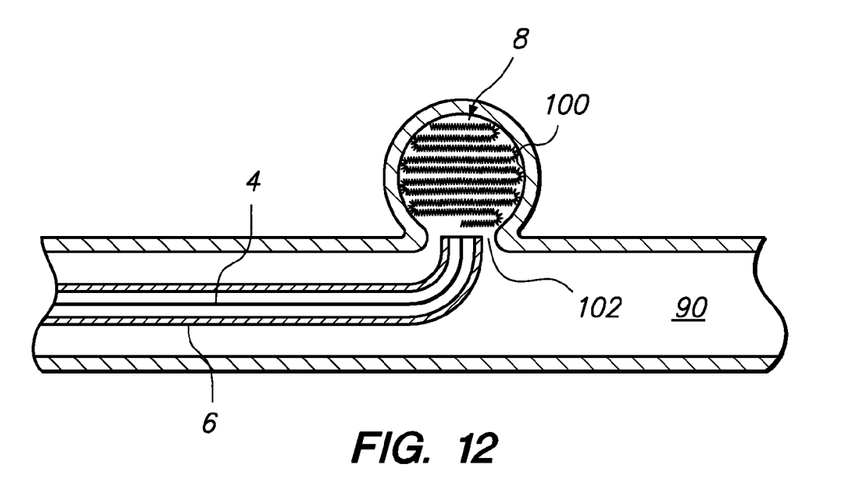
FIG. 12 is a cross-sectional side view of the vascular region of FIG. 11 illustrating the coil being completely detached from the delivery member.

With the delivery member 4 and coil 14 secured to one another, the coil 14 can then be maneuvered into position for deployment within the intended vascular space (e.g., aneurysm 100 as shown in FIGS. 11 and 12). FIGS. 11 and 12, for example, illustrate the deployment of a vaso-occlusive device 8 within an aneurysm 100. To deploy or detach the coil 14 from the delivery member 4, a direct current of opposite polarity (opposite with respect to the polarity used to expand the actuating member 10) is applied to the actuating member 10. The actuating member 10 then converts to the non-expanded state (e.g., as shown in FIGS. 2, 2A, and 4).

Because this procedure takes place with the vasculature of the patient, the actuating member 10 is in contact with bodily fluids such as blood that contains the ionic species needed to alter the shape of the EAP layer 26. In the non-expanded state, the coil 14 is then free of the delivery member 4. The delivery member 4 and surrounding catheter 6 can then be withdrawn from vasculature of the patient.

Figure 8:
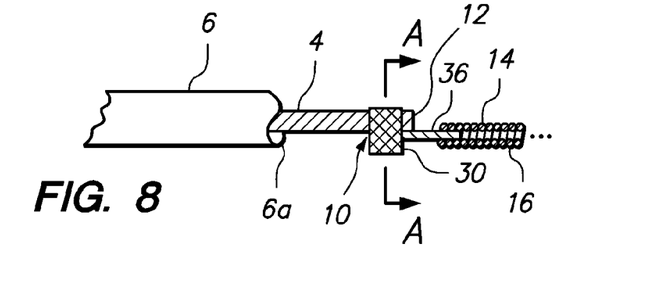
FIG. 8 is a side view of an elongate delivery member that is secured to a vaso-occlusive coil via a mating member. The bilayer member located at the distal end of the delivery member is in the biased, closed state.
Figure 8A:
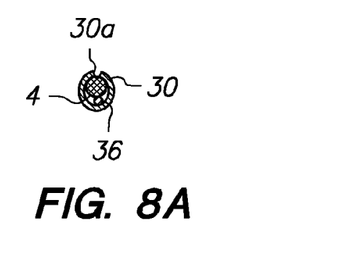
FIG. 8A is a cross-sectional view of the elongate delivery member and bilayer actuating member taken along the line A-A in FIG. 8.
Figure 9:
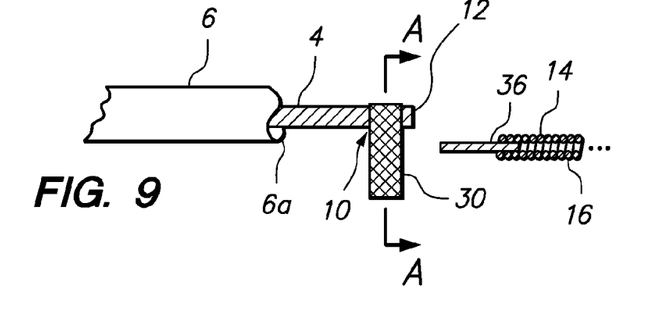
FIG. 9 is a slide view of an elongate delivery member that is detached from the vaso-occlusive coil and mating member. The bilayer member located at the distal end of the delivery member is in the biased, open state.
Figure 9A:
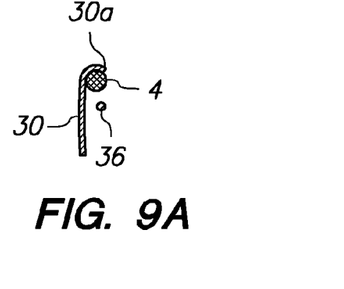
FIG. 9A is a cross-sectional view of the elongate delivery member and bilayer actuating member taken along the line A-A in FIG. 9.
Figure 10:
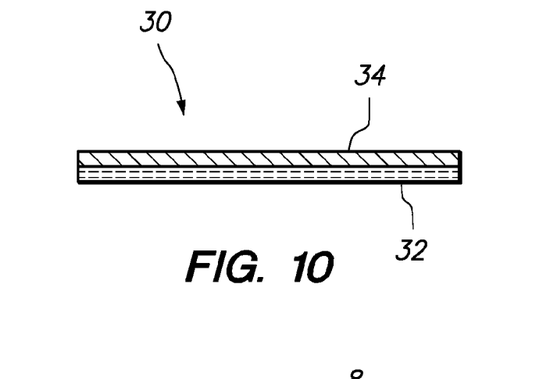
FIG. 10 is a side view of a bilayer member according to one aspect of the invention.

FIGS. 6, 6A, 7, 7A, 8, 8A, 9, and 9A, and 10 illustrate a delivery device 2 according to an alternative embodiment of the invention. In this alternative embodiment, the actuating member 10 is formed as a bilayer member 30. As best seen in FIG. 10 the bilayer member 30 has a first layer 32 formed from a material that does not appreciably change in volume in response to an applied electrical current. As one example, the first layer 32 may be formed from a metallic material. The bilayer member 30 includes a second layer 34 formed from an electroactive polymer. The EAP may be formed from any electroactive polymer including, without limitation, those specifically set forth above.

Figure 6:
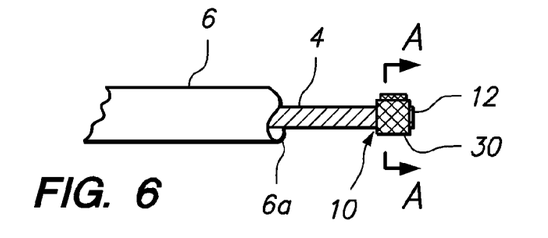
FIG. 6 is a side view of an elongate delivery member according to another embodiment of the invention. The elongate delivery member is shown with a bilayer actuating member disposed at a distal end of the delivery member. The bilayer member is shown in a biased, closed state.
Figure 6A:
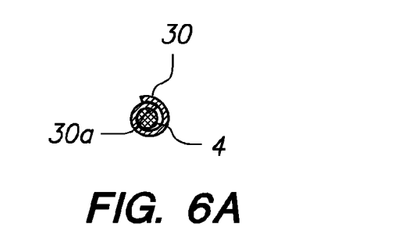
FIG. 6A is cross-sectional view of the elongate delivery member and bilayer actuating member taken along the line A-A in FIG. 6.
Figure 7:
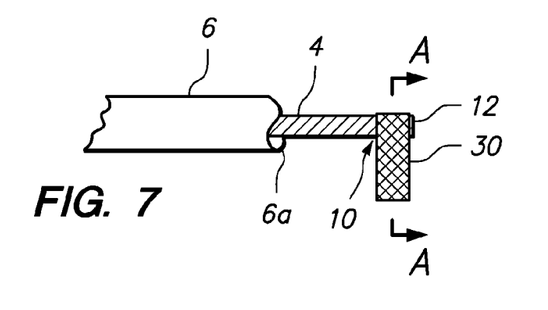
FIG. 7 is a side view of an elongate delivery member according to another embodiment of the invention. The elongate delivery member is shown with a bilayer actuating member disposed at a distal end of the delivery member. The bilayer member is shown in a biased, open state.
Figure 7A:
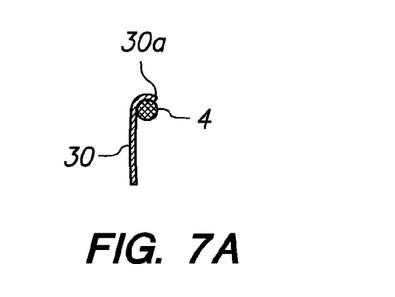
FIG. 7A is cross-sectional view of the elongate delivery member and bilayer actuating member taken along the line A-A in FIG. 7.

Referring now to FIGS. 6, 6A, 7, and 7A, an elongate delivery member 4 is illustrated with bilayer member 30 disposed substantially at the distal end 12 thereof. Alternatively, the bilayer member 30 may be disposed adjacent to the distal end 12 of the delivery member 4. As best seen in FIGS. 6A and 7A, the bilayer member 30 has one end 30a fixedly secured to the delivery member 4. The bilayer member 30 may be secured to the delivery member 4 via a weld, braze, adhesive, or other fixation method generally known to those skilled in the art. FIG. 6 and 6A illustrate the bilayer member 30 in a first (e.g., closed) biased state. Upon application of a direct current to the EAP layer 34, the bilayer member 30 bends or coils upon itself to assume a closed configuration around the delivery member 4.

Depending on the location of the EAP layer 34, the bending may be caused by either a contraction or expansion of the EAP layer 34. For example, if the EAP layer 34 is located out the outside of the bilayer member 30 (in the radial direction), expansion of the EAP layer 34 will cause the bilayer member 30 to coil around the delivery member 4. Alternatively, the same coiling effect may be achieved if the EAP layer 34 is located on the inner side of the bilayer member 30 and is exposed to a direct current that causes contraction of the EAP layer 34. Regardless of the location of the EAP layer 34 on the bilayer member 30, a biasing direct current is applied to the bilayer member 30 to actuate the bilayer member 30 into the closed state shown in FIGS. 6 and 6A. The biasing current may be a direct current having a first polarity (e.g., positive or negative).

FIGS. 7 and 7A illustrate the bilayer member 30 biased in a second open state. In the open state, the bilayer member 30 is no longer coiled or wrapped around the delivery member 4. Instead, the bilayer member 30 forms an arcuate or straight configuration. It should be understood, however, that an "open" biased state may be formed without having the bilayer member 30 completely open as is shown in FIGS. 7 and 7A. For example, a partially coiled or wound state may suffice for releasing the delivery member 4 as is described in more detail below.

Referring now to FIGS. 8 and 8A, the delivery member 4 with the bilayer member 30 is shown secured to a vaso-occlusive device 8. A vaso-occlusive device 8 in the form of a helically wound coil 14 includes a mating member 36 secured in a proximal end 16 of the coil 14. In one embodiment, the mating member 36 is formed as a rod or projection around which the bilayer member 30 is secured when in the closed state. Alternatively, the mating member 36 may have one or more surfaces formed to assist in securing the coil 40 to the delivery member 4. For example, a portion of the mating member 36 may be arcuate shaped to better conform to the exterior of the delivery member 4.

As shown in FIGS. 8 and 8A, the bilayer member 30 physically contacts the mating member 36 an mechanically secures the mating member 36 to the delivery member 4. For example, in one aspect of the invention, the mating member 36 is pinched between the bilayer member 30 and delivery member 4. In this regard, the coil 14 is then fixedly secured to the delivery member 4. To affix the coil 14 to the delivery member 4, the mating member 36 is placed in an overlapping arrangement with the delivery member 4 with the bilayer member 30 in the open configuration or state. The bilayer member 30 is then actuated by application of a biasing direct current of a first polarity (e.g., positive or negative) to transform or toggle the bilayer member 30 from the open state to the closed state. The bilayer member 30 then coils or wraps around the mating member 36 and delivery member 4 to secure the coil 14. This loading operation may be performed in the presence of an ionic environment to permit the passage of ionic species into and out of the EAP layer 34.

FIGS. 9 and 9A illustrate the bilayer member 30 biased to the open state. In this configuration, the mating member 36 is no longer secured to the delivery member 4. Consequently, to release the vaso-occlusive device 8 within a vascular space such as an aneurysm, a biasing direct current is delivered to the bilayer member 30 to cause the same to transition from the closed state (e.g., shown in FIGS. 8 and 8A) to an open state shown in FIGS. 9 and 9A. Upon the opening of the bilayer member 30 the coil 14 is free from the delivery member 4 and is thus able to fill the void or space within the site of interest.

FIG. 11 illustrates a cross-sectional representation of a delivery device 2 delivering a vaso-occlusive device 8 to vascular site of interest such as, for example, an aneurysm 100. To reach the aneurysm 100, the catheter 6 or the like containing the vaso-occlusive device 8 is advanced through a blood vessel 90. Typically, the catheter 6 is advanced or otherwise steered such that the distal tip 6a is in close proximity with a neck 102 of the aneurysm 100. At this stage the primary coil 14 is contained with the catheter 6 and is coupled at the proximal end 16 to the delivery member 4 such as a core wire. Once the delivery device 2 is in place, the delivery member 4 (e.g., core wire) is then pushed toward the distal tip 6a of the catheter 6 causing the coil 14 to extend out of the distal tip 6a of the catheter 6, through the neck 102, and into the aneurysm 100. As the coil 14 is pushed out of the catheter 6, the portion of the coil 14 that is free from the restraints of the catheter 6 can assume its deployed or secondary shape as is shown in FIG. 11.

Turning to FIG. 12, the delivery member 4 is then separated from the, coil 14. In the case of the embodiment illustrated in FIGS. 1, 1A, 2, 2A, 3, 3A, 4, and 5, the actuating member 10 is actuated by application of a biasing direct current to transform the actuating member 10 to its non-expanded state. The direct current may be applied to the actuating member 10, for example, via the delivery member 4 (e.g., core wire). Alternatively, direct current may be applied via a separate dedicated conductor (not shown). The transformation of the actuating member 10 to the non-expanded state separates the delivery member 4 from the proximal end 16 of the coil 14. Upon separation, the coil 14 can assume the fully deployed state as is shown in FIG. 12.

In the alternative embodiment illustrated in FIGS. 6, 6A, 7, 7A, 8, 8A, 9, and 9A, a direct current is applied to the bilayer member 30 to cause the same to transform into an open state. As in the prior embodiment, the direct current may be applied via the delivery member 4 or a dedicated conducting member. When the bilayer member 30 transitions to the open state, the mating member 36 separates from the delivery member 4 and the coil 14 is able to assume the fully deployed state (e.g., FIG. 12).

While embodiments of the present invention have been shown and described, various modifications may be made without departing from the scope of the present invention. The invention, therefore, should not be limited, except to the following claims, and their equivalents.

What is claimed is:

1. A vaso-occlusive delivery device comprising:

an elongate delivery member having a distal end;

an actuating member disposed at or adjacent to the distal end of the elongate delivery member, the actuating member including an electroactive polymer, wherein the electroactive polymer is biased to a first state upon application of DC current of a first polarity and biased to a second state upon application of a DC current of a second, opposite polarity; and a coil having a tubular member disposed inside the coil, the tubular member having an inner surface defining a lumen, wherein when the actuating member is in the first biased state, the actuating member forms an interference fit with the inner surface of the tubular member and when the actuating member is in the second biased state the actuating member is detached from the tubular member.

2. The vaso-occlusive delivery device of claim 1, wherein the first biased state is an expanded state and the second biased state is a non-expanded state.

3. The vaso-occlusive delivery device of claim 1, the actuating member further comprising an actuating ring disposed between the elongate delivery member and the electroactive polymer.

4. The vaso-occlusive delivery device of claim 3, wherein the actuating ring comprises a metallic material.

5. The vaso-occlusive delivery device of claim 1, wherein the electroactive polymer comprises polypyrrole.

6. The vaso-occlusive delivery device of claim 1, wherein the elongate delivery member comprises core wire.

7. The vaso-occlusive delivery device of claim 1, wherein the actuating member comprises a radially expandable ring.

* * * * *